(12) United States Patent
Minakuchi

(10) Patent No.: US 9,979,204 B2
(45) Date of Patent: *May 22, 2018

(54) LOAD VOLTAGE CONTROL DEVICE, ELECTRONIC ENDOSCOPE AND ELECTRONIC ENDOSCOPE SYSTEM

(71) Applicant: HOYA CORPORATION, Tokyo (JP)

(72) Inventor: Tadashi Minakuchi, Saitama (JP)

(73) Assignee: HOYA CORPORATION, Tokyo (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/455,288

(22) Filed: Mar. 10, 2017

(65) Prior Publication Data
US 2017/0187195 A1  Jun. 29, 2017

Related U.S. Application Data

(63) Continuation of application No. 14/645,797, filed on Mar. 12, 2015, now Pat. No. 9,627,960.

(30) Foreign Application Priority Data

Mar. 31, 2014 (JP) ................... 2014-071142

(51) Int. Cl.
*H02J 4/00* (2006.01)
*A61B 1/04* (2006.01)
(Continued)

(52) U.S. Cl.
CPC ............ *H02J 4/00* (2013.01); *A61B 1/00027* (2013.01); *A61B 1/04* (2013.01); *G02B 23/2484* (2013.01);
(Continued)

(58) Field of Classification Search
None
See application file for complete search history.

(56) References Cited

U.S. PATENT DOCUMENTS 4,860,095 A * 8/1989 Kimura ............... A61B 1/05
 348/241
7,502,062 B2 * 3/2009 Suda ................... H04N 5/335
 348/298

(Continued)

FOREIGN PATENT DOCUMENTS

| JP | 1-132280 | 5/1989 |
| JP | 2009-106442 | 5/2009 |
| JP | 2013-44807 | 3/2013 |

*Primary Examiner* — Reza Aghevli
(74) *Attorney, Agent, or Firm* — Greenblum & Bernstein, P.L.C.

(57) ABSTRACT

A load voltage control device, comprising: a load disposed in a tip portion; a power supply circuit and a controller disposed in a proximal end portion; and a cable connecting the tip portion with the proximal end portion, the cable comprising a first and second power supply lines, the power supply circuit comprising at least one power supply, wherein the controller operates to: obtain a voltage applied to the load based on a voltage applied to an input point of the first power supply line, a current flowing through the first power supply line, a voltage applied to an input point of the second power supply line and a current flowing through the second power supply line; and adjust the power supply voltage by controlling the at least one power supply so that the voltage applied to the load becomes substantially equal to a predetermined reference voltage.

6 Claims, 6 Drawing Sheets

(51) Int. Cl.
    *A61B 1/00*     (2006.01)
    *H04N 5/225*     (2006.01)
    *G02B 23/24*     (2006.01)

(52) U.S. Cl.
    CPC ... *H04N 5/2257* (2013.01); *H04N 2005/2255* (2013.01)

(56) References Cited

U.S. PATENT DOCUMENTS

| | | | |
|---|---|---|---|
| 7,593,051 B2* | 9/2009 | Suda | H04N 5/335 348/311 |
| 8,243,172 B2* | 8/2012 | Usami | A61B 1/00059 348/192 |
| 2006/0223637 A1* | 10/2006 | Rosenberg | A63F 13/10 463/47 |
| 2013/0030248 A1* | 1/2013 | Matsumaru | A61B 1/00027 600/110 |
| 2016/0211887 A1 | 7/2016 | Williams | |

* cited by examiner

LOAD VOLTAGE CONTROL DEVICE, ELECTRONIC ENDOSCOPE AND ELECTRONIC ENDOSCOPE SYSTEM

This is a continuation application of pending U.S. patent application Ser. No. 14/645,797, filed Mar. 12, 2015, which claims priority to Japanese Application No. 2014-071142, filed Mar. 31, 2014, The disclosures of these documents, including the specifications, drawings and claims, are incorporated herein by reference in their entirety.

BACKGROUND OF THE INVENTION

The present invention relates to a load voltage control device which controls a voltage supplied to a load, and more specifically to a load voltage control device which controls a voltage supplied to a load via a cable, an electronic endoscope and an electronic endoscope system.

Conventionally, electronic endoscopes capable of observing and capturing a target portion by inserting a long slender insertion unit into a body cavity of a patient have been widely used. In an electronic endoscope of this type, an image pickup device (e.g., a CCD image sensor or a CMOS image sensor) for capturing the inside of a body cavity is disposed in a tip portion of the insertion unit. Supplying of a power supply voltage to the image pickup device is performed via a long cable from a power supply circuit disposed in a proximal end portion of the electronic endoscope (i.e., a connection part to a video processor) or disposed in a video processor. In this case, a voltage drop by the cable may affect image capturing and cannot be neglected. Therefore, a designer may consider configuring a power supply circuit to generate a power supply voltage to which a voltage corresponding to the voltage drop is added in advance, and to supply the power supply voltage to an image pickup device. However, the length and specifications (e.g., electric resistance) of a cable connecting the power supply circuit with the tip portion of the electronic endoscope varies depending on the type of the electronic endoscope. Further, the loss caused by the cable also varies depending on the type of the electronic endoscope.

Japanese Patent Provisional Publication No. 2009-106442A (hereafter, referred to as patent document 1) suggests technology for solving the above described problem. In an endoscope described in patent document 1, a correction value corresponding to a property of a cable is stored in advance in a memory, and a signal transmitted to an image pickup device is corrected (e.g., amplification) based on the correction value.

SUMMARY OF THE INVENTION

However, regarding the endoscope described in patent document 1, it is necessary to measure the property of the cable and to store the measured property in advance, which is very troublesome work. Furthermore, it is difficult to cope with variations in the cable length and the property among products. Furthermore, it is impossible to adjust the power supply voltage depending on, for example, an operating status (e.g., change of a consumption current) of the image pickup device.

A designer might consider implementing feedback control by disposing a detection unit for detecting a voltage applied to the image pickup device in the tip portion. However, this is not suitable in regard to keeping the tip portion compact.

The present invention is advantageous in that it provides a load voltage control device, an electronic endoscope and an electronic endoscope system capable of supplying an appropriate voltage to a load regardless of the cable length or specifications.

According to an aspect of the invention, there is provided a load voltage control device, comprising: a load disposed in a tip portion of the load voltage control device; a power supply circuit disposed in a proximal end portion of the load voltage control device; a controller disposed in the proximal end portion of the load voltage control device; and a cable connecting the tip portion with the proximal end portion. The cable comprises a first power supply line and a second power supply line, both of which serve to transmit a power supply voltage to the load. The power supply circuit comprises at least one power supply that generates the power supply voltage and outputs the power supply voltage to the first power supply line and the second power supply line. In this configuration, the controller operates to: obtain a voltage applied to the load based on a voltage applied to an input point of the first power supply line, a current flowing through the first power supply line, a voltage applied to an input point of the second power supply line and a current flowing through the second power supply line; and adjust the power supply voltage generated by the at least one power supply by controlling the at least one power supply so that the voltage applied to the load becomes substantially equal to a predetermined reference voltage.

With this configuration, it becomes possible to obtain, in a power supply circuit, a voltage applied to a load, and thereby it becomes possible to supply a power supply voltage having a high degree of accuracy to the load regardless of a cable length and specifications. Furthermore, it becomes possible to stably drive the load. Furthermore, by providing a plurality of power supply lines, a voltage drop can be reduced.

The at least one power supply may comprise a first power supply and a second power supply. In this case, the first power supply line may be connected to the first power supply, and the second power supply line may be connected to the second power supply.

The at least one power supply may be a single power supply. In this case, the power supply circuit may further comprise: a first resistor provided between the first power supply line and the single power supply; and a second resistor provided between the second power supply line and the single power supply. Resistance values of the first resistor and the second resistor may be different from each other.

The power supply circuit may further comprise: a first capacitor provided at a connection point between the first power supply line and the first resistor; and a second capacitor provided at a connection point between the second power supply line and the second resistor.

The first power supply line and the second power supply line may be formed of a same wiring material having a same length and same specifications.

The controller may obtain the voltage applied to the load based on a following expression:

$$V_L = (I_2 \times V_1 - I_1 \times V_2)/(I_2 - I_1)$$

where $V_L$ denotes the voltage applied to the load, $V_1$ denotes the voltage applied to the input point of the first power supply line, $I_1$ denotes the current flowing through the first power supply line, $V_2$ denotes the voltage applied to the input point of the second power supply line and $I_2$ denotes the current flowing through the second power supply line.

The controller may obtain the voltage applied to the load based on a following expression:

$$V_L=(n\times m\times I_2\times V_1-I_1\times V_2)/(n\times m\times I_2-I_1)$$

where $V_L$ denotes the voltage applied to the load, $V_1$ denotes the voltage applied to the input point of the first power supply line, $I_1$ denotes the current flowing through the first power supply line, $V_2$ denotes the voltage applied to the input point of the second power supply line, $I_2$ denotes the current flowing through the second power supply line, n denotes a ratio of a loss per a unit length between the first power supply line and the second power supply line and m denotes a ratio of a length between the first power supply line and the second power supply line.

The cable may further comprise a third power supply line that supplies the power supply voltage to the load.

According to another aspect of the invention, there is provided an electronic endoscope, comprising: a load including an image pickup device and disposed in a tip portion of the electronic endoscope; a power supply circuit disposed in a proximal end portion of the electronic endoscope; a controller disposed in the proximal end portion of the electronic endoscope; and a cable connecting the tip portion with the proximal end portion. The cable comprises a first power supply line and a second power supply line, both of which serve to transmit a power supply voltage to the load. The power supply circuit comprises at least one power supply that generates the power supply voltage and outputs the power supply voltage to the first power supply line and the second power supply line. In this configuration, the controller operates to: obtain a voltage applied to the load based on a voltage applied to an input point of the first power supply line, a current flowing through the first power supply line, a voltage applied to an input point of the second power supply line and a current flowing through the second power supply line; and adjust the power supply voltage generated by the at least one power supply by controlling the at least one power supply so that the voltage applied to the load becomes substantially equal to a predetermined reference voltage.

With this configuration, it becomes possible to supply a power supply voltage having a high degree of accuracy to a load regardless of a cable length and specifications, and thereby it becomes possible to stably drive the load.

According to another aspect of the invention, there is provided an electronic endoscope system, comprising: a processor comprising a power supply circuit and a controller; and an electronic endoscope connected to the processor. The electronic endoscope comprises: a load including an image pickup device; and a cable connecting the load with the power supply circuit of the processor. The cable comprises a first power supply line and a second power supply line, both of which serve to transmit a power supply voltage to the load. The power supply circuit comprises at least one power supply that generates the power supply voltage and outputs the power supply voltage to the first power supply line and the second power supply line. The controller operates to: obtain a voltage applied to the load based on a voltage applied to an input point of the first power supply line, a current flowing through the first power supply line, a voltage applied to an input point of the second power supply line and a current flowing through the second power supply line; and adjust the power supply voltage generated by the at least one power supply by controlling the at least one power supply so that the voltage applied to the load becomes substantially equal to a predetermined reference voltage.

With this configuration, it becomes possible to supply a power supply voltage having a high degree of accuracy to a load regardless of a cable length and specifications, and thereby it becomes possible to stably drive the load.

BRIEF DESCRIPTION OF THE ACCOMPANYING DRAWINGS

DETAILED DESCRIPTION OF THE EMBODIMENTS

Hereinafter, embodiments of the invention, embodied as an electronic endoscope system provided with a load voltage control device, are described by way of example with reference to the accompanying drawings.

First Embodiment

Figure 1:
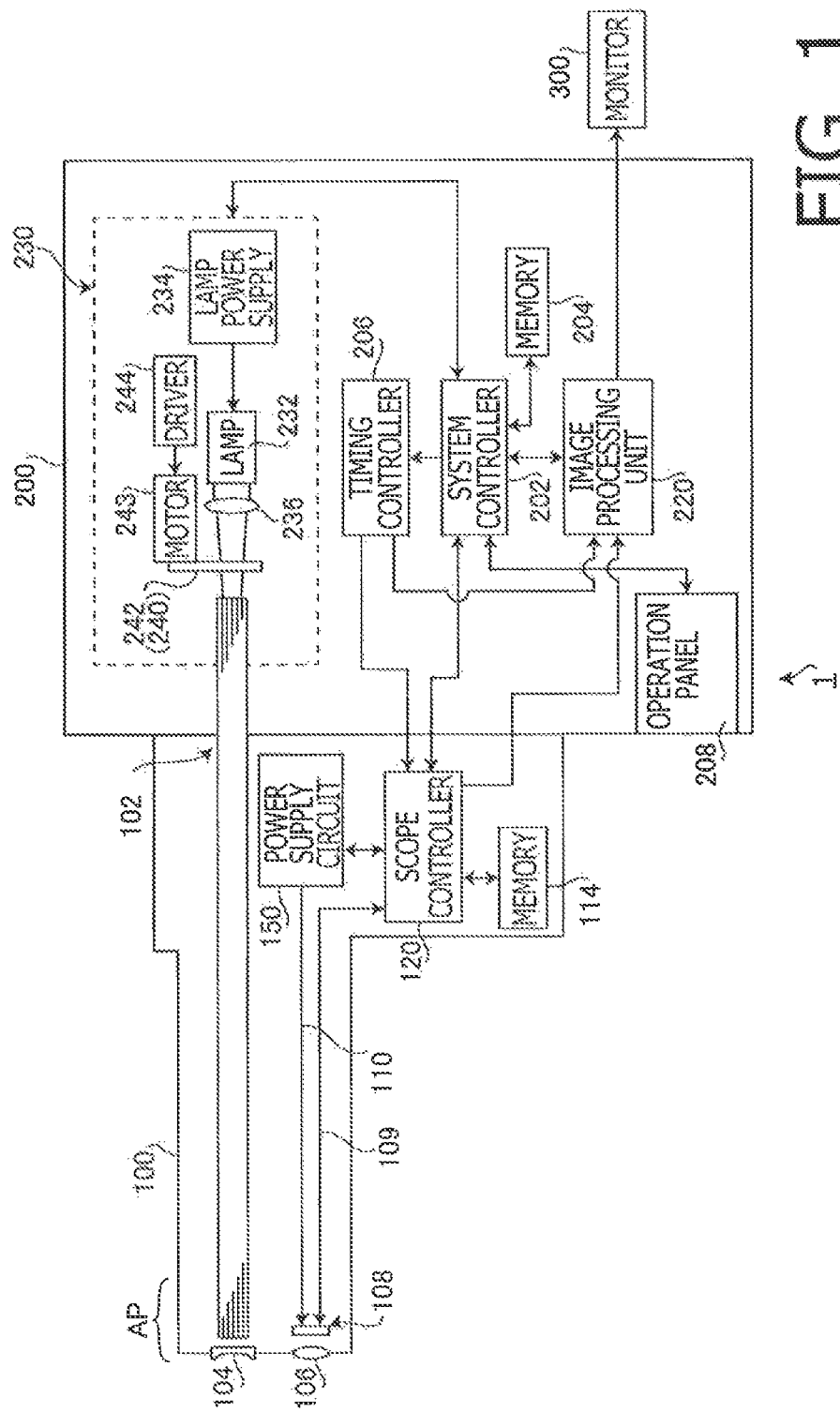
FIG. 1 is a block diagram generally illustrating a configuration of an electronic endoscope system according to a first embodiment of the invention.

FIG. 1 is a block diagram generally illustrating a configuration of an electronic endoscope system 1 according to a first embodiment of the invention. As shown in FIG. 1, the electronic endoscope system 1 includes an electronic endoscope 100, an electronic endoscope processor 200 and a monitor 300.

The electronic endoscope processor 200 includes a system controller 202 and a timing controller 206. The system controller 202 totally controls the entire electronic endoscope system 1 by executing various programs stored in a memory 204. Further, the system controller 202 changes various settings of the electronic endoscope system 1 in response to an instruction from a user (an operator or an assistant) input to an operation panel 208. The timing controller 206 outputs clock pulses for adjusting operation timings of respective parts to various circuits in the electronic endoscope system 1.

The electronic endoscope processor 200 includes a light source 230 which supplies illumination light being a white light beam to an LCB (Light Carrying Bundle) 102 of the electronic endoscope 100, The light source 230 includes a lamp 232, a lamp power supply 234, a condenser lens 236 and a dimmer control device 240. The lamp 232 is a high luminance lamp which emits the illumination light by being supplied driving power from the lamp power supply 234, and is, for example, a xenon lamp, a metal halide lamp, a mercury lamp or a halogen lamp. The illumination light emitted by the lamp 232 is converged by the condenser lens 236, and then is guided to the LCB 102 via the dimmer control device 240.

The dimmer control device 240 adjusts the light amount of the illumination light guided to the LCB 102 under control of the system controller 202, and includes an aperture stop 242, a motor 243 and a driver 244. The driver 244 generates a driving current for driving the motor 243, and supplies the driving current to the motor 243. The aperture stop 242 is driven by the motor 243 to change the opening through which the illumination light passes, and thereby to adjust the light amount of the illumination light passing through the opening.

The illumination light guided to the LCB 102 via an entrance end of the LCB 102 propagates through the LCB 102, exits from an exit end of the LCB 102 disposed at a tip of the electronic endoscope 100, and illuminates a subject via a light distribution lens 104. Reflected light from the subject forms an optical image on a light-receiving surface of an image pickup device 108.

A power supply circuit 150 supplies, via a cable 110, a power supply voltage to a load, such as the image pickup device 108, disposed at a tip portion AP of the electronic endoscope 100. The image pickup device 108 is, for example, a single-ship color CCD (Charge-Coupled Device) image sensor provided with various types of filters on a light-receiving surface thereof. In accordance with a control signal transmitted from a scope controller 120 via a cable 109, the image pickup device 108 generates an imaging signal of each of colors of a color filter according to the optical image converged on the light-receiving surface. The generated imaging signal is converted into a digital image signal in the scope controller 120, and is transmitted to an image processing unit 220 of the electronic endoscope processor 200. The scope controller 120 accesses a memory 114 (e.g., a ROM or a non-volatile memory) to read unique information of the electronic endoscope 100. The unique information of the electronic endoscope 100 recorded in the memory 114 includes, for example, the number of pixels, sensitivity and operable frame rates. The scope controller 120 outputs the unique information read from the memory 114 to the system controller 202.

The system controller 202 executes various operations based on the unique information of the electronic endoscope 100, and generates control signals. Using the generated control signals, the system controller 202 controls operation and timings of the various circuits in the electronic endoscope processor 200 so that processing suitable for the electronic endoscope 100 connected to the electronic endoscope processor 200 can be executed. The timing controller 206 supplies the clock pulses to the scope controller 120 and the image processing unit 220 in accordance with timing control by the system controller 202.

Under control of the system controller 202, the image processing unit 220 of the electronic endoscope processor 200 generates a video signal for monitor representation of an endoscopic image based on the image signal transmitted from the scope controller 120 of the electronic endoscope 100, and outputs the video signal to the monitor 300. The operator is able to observe or treat, for example, a digestive tube, while checking an endoscopic image displayed on the monitor 300.

Figure 2:
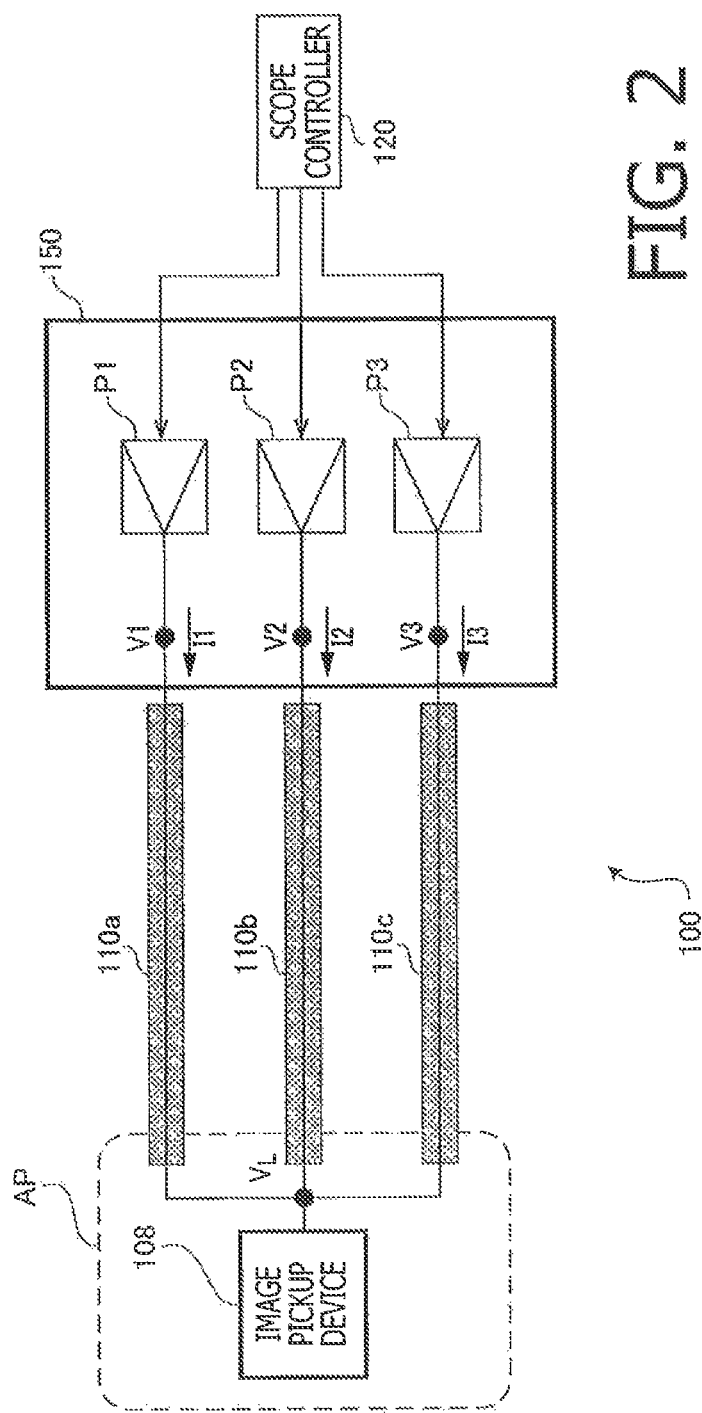
FIG. 2 illustrates a configuration of a power supply circuit according to the first embodiment of the invention.

Hereafter, control of the power supply voltage by the power supply circuit 150 according to the embodiment is explained with reference to FIG. 2. FIG. 2 illustrates a configuration of the power supply circuit 150 according to the embodiment. As shown in FIG. 2, the power supply circuit 150 includes a first power supply P1, a second power supply P2 and a third power supply P3. A power supply voltage $V_1$ generated by the first power supply P1 is supplied to the image pickup device 108 via a first power supply line 110a. A power supply voltage $V_2$ generated by the second power supply P2 is supplied to the image pickup device 108 via a second power supply line 110b. A power supply voltage $V_3$ generated by the third power supply P3 is supplied to the image pickup device 108 via a third power supply line 110c. The first power supply P1, the second power supply P2 and the third power supply P3 are controlled respectively by the scope controller 120. It should be noted that in this embodiment the voltage $V_1$ is different from the voltage $V_2$.

Since each of the power supply lines 110a, 110b and 110c is a long cable (e.g., having a length of several meters), a voltage drop is caused on a voltage $V_L$ applied to the image pickup device 108. The losses by the power supply lines 110a, 110b and 110c vary depending on the length of a cable or specifications, and change of consumption current in circuit operation of the tip portion AP. Therefore, even when the consumption current of the image pickup device 108 and the loss of the power supply line 110a are calculated preliminary from the specifications at the design stage, it is difficult to obtain the accurate voltage $V_L$.

Focusing on a system of the first power supply P1, the voltage $V_L$ applied to the image pickup device 108 is represented by the following expression (1).

$$V_L = V_1 - R_1 \times I_1 \tag{1}$$

where $R_1$ denotes the loss of the first power supply line 110a, and is obtained by the following expression (2) when $r_1$ denotes a loss per a unit length of the first power supply line 110a and $L_1$ denotes the length the first power supply line 110a.

$$R_1 = r_1 \times L_1 \tag{2}$$

Focusing on a system of the second power supply P2, the voltage $V_L$ applied to the image pickup device 108 is represented by the following expression (3).

$$V_L = V_2 - R_2 \times I_2 \tag{3}$$

where $R_2$ denotes the loss of the second power supply line 110b, and is obtained by the following expression (4) when $r_2$ denotes a loss per a unit length of the second power supply line 110b and $L_2$ denotes the length the second power supply line 110b.

$$R_2 = r_2 \times L_2 \tag{4}$$

When $r_2 = n \times r_1$ and $L_2 = m \times L_1$ and the expressions (1) to (3) are solved for $V_L$, the following expression (5) is obtained. In this case, n is a ratio of "a loss per a unit line" between the first power supply line 110a and the second power supply line 110b, and m denotes a ratio of "length" between the first power supply line 110a and the second power supply line 110b.

$$V_L = (n \times m \times I_2 \times V_1 - I_1 \times V_2)/(n \times m \times I_2 - I_1) \tag{5}$$

In this embodiment, the wiring material having the same specifications is used for both of the first power supply line 110a and the second power supply line 110b. Therefore, in this embodiment, n=m=1 and the voltage $V_L$ is expressed by the following expression (6).

$$V_L = (I_2 \times V_1 - I_1 \times V_2)/(I_2 - I_1) \tag{6}$$

Therefore, in this embodiment, by obtaining the voltage $V_1$ applied to the first power supply line 110a and the current $I_1$ flowing through the first power supply line 110a and by assigning the obtained values to the above described expression (6), the voltage $V_L$ actually applied to the image pickup device 108 can be obtained. The scope controller 120 obtains the voltage $V_L$ actually applied to the image pickup device 108 using the above described expression (6), and adjusts one of the voltage $V_1$, the current $I_1$, the voltage $V_2$ and the current $I_2$ by controlling the first power supply P1 and/or the second power supply P2 so that the voltage $V_L$ becomes equal to the reference voltage Vref. It should be noted that the reference voltage Vref is a rated voltage of the image pickup device 108. The reference voltage Vref may be set, for example, based on the unique information of the electronic endoscope 100 read from the memory 114.

As an example of control of the first power supply P1 and/or the second power supply P2, first the voltage $V_1$ generated by the first power supply P1 is fixed. Then, the current $I_1$ flowing through the first power supply line 110a and the current $I_2$ flowing through the second power supply line 110b are detected by a current detector (not shown). The scope controller 120 adjusts the voltage $V_2$ by controlling the second power supply P2 so that the voltage $V_L$ applied to the image pickup device 108 becomes equal to the rated voltage Vref or falls within a specification value range, while assigning the voltage $V_1$, the current $I_1$, the voltage $V_2$ and the current $I_2$ to the above described expression (6). For example, when the voltage $V_L$ obtained from the expression (6) is larger than the rated voltage Vref of the image pickup device 108, the voltage $V_2$ is decreased. Then, the voltage $V_L$ is obtained again from the expression (6), and is compared with the rated voltage Vref. Then, in accordance with the comparison results, the voltage $V_2$ is increased or decreased until the voltage $V_L$ becomes equal to the rated voltage Vref or falls within the specification value range.

In this embodiment, the length and the specifications of the third power supply line may be arbitrarily set, and the output voltage $V_3$ and the current I3 of the third power supply P3 are set appropriately depending on the power supplied to the image pickup device 108.

As described above, in this embodiment, by providing a plurality of power supply lines for transmitting the power supply voltage, the voltage $V_L$ actually applied to the image pickup device 108 can be obtained on the proximal end side (i.e., by the scope controller 120) of the electronic endoscope 100. As a result, it becomes possible to stably drive the image pickup device 108 while applying the voltage $V_L$ having a high degree of accuracy to the image pickup device 108, regardless of the type of the electronic endoscope 100 (e.g., the length and the specifications of cables). Furthermore, since the voltage drop on the power supply line can be reduced by using a plurality of power supply lines, it is not necessary to heighten the output power supply voltage.

Furthermore, in this embodiment, all of the cables connecting the power supply circuit 150 to the image pickup device 108 are used as the power supply lines, efficiency in power supply can be enhanced in comparison with the case where a signal line or the like for detecting the voltage $V_L$ applied to the image pickup device 108 and thereby performing feedback is separately provided. As a result, it becomes also possible to supply a large power to the image pickup device 108 while preventing increase of the diameter of the power supply line.

Second Embodiment

Hereafter, an electronic endoscope 100A according to a second embodiment of the invention is described. In the electronic endoscope 100A according to the second embodiment, only a configuration of a power supply circuit 150A is different from the first embodiment, and the other configurations in the second embodiment are the same as those of the first embodiment. Therefore, in the following, explanations about the second embodiment focus on the feature of the second embodiment. In the following, to elements which are substantially the same as those of the first embodiment, the same reference numbers are assigned and explanations thereof will not be repeated.

Figure 3:
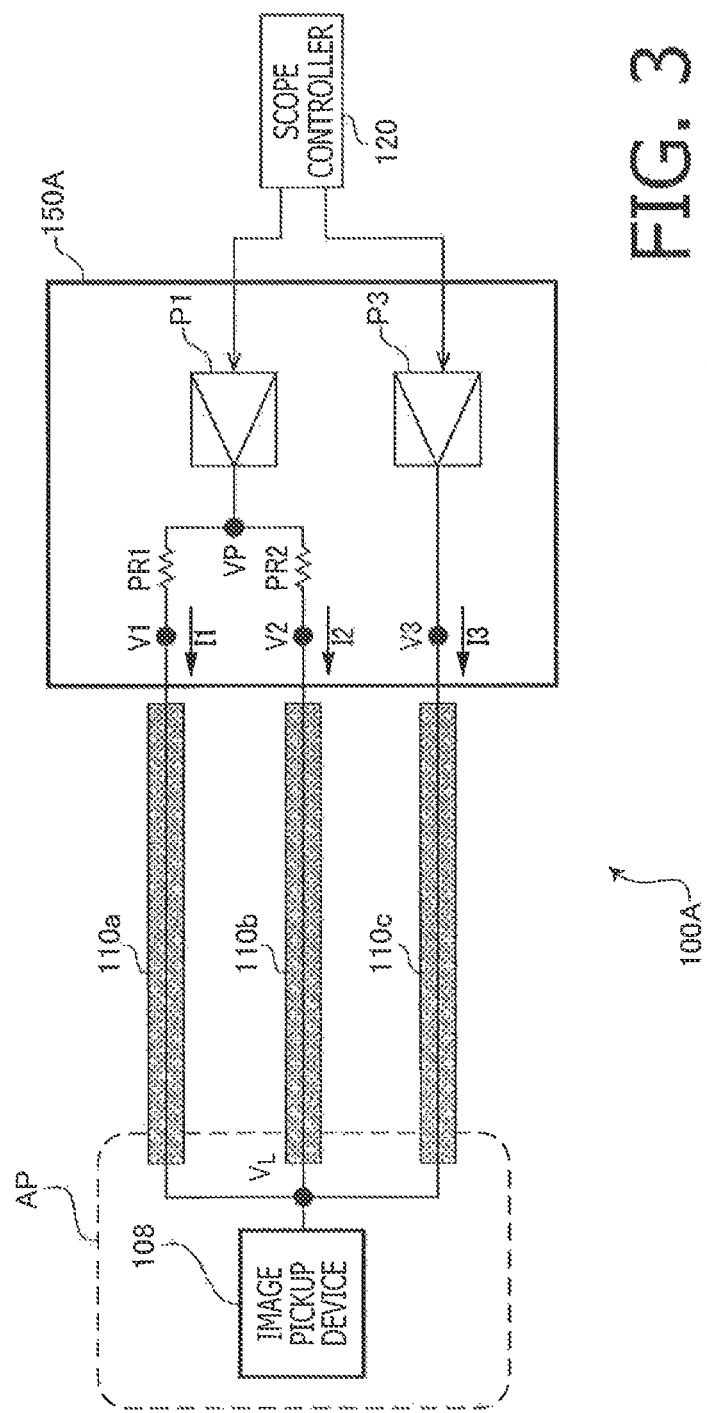
FIG. 3 illustrates a configuration of a power supply circuit according to a second embodiment of the invention.

FIG. 3 illustrates a configuration of the power supply circuit 150A according to the second embodiment. As shown in FIG. 3, the power supply circuit 150A includes the first power supply P1 and the third power supply P3. In the second embodiment, the power supply lines 110a and 110b are connected to the first power supply P1 (i.e., one power supply). The voltage VP generated by the first power supply P1 is transmitted to the image pickup device 108 via the power supply lines 110a and 110b. The voltage $V_3$ generated by the third power supply P3 is transmitted to the image pickup device 108 via the power supply line 110c. The first power supply P1 and the third power supply P3 are controlled by the scope controller 120.

Specifically, the first power supply P1 is connected to the first power supply line 110a via a first resistor PR1, and is connected to the second power supply line 110b via a second resistor PR2. Resistances of the first resistor PR1 and the second resistor PR2 are different from each other (PR1≠PR2). Therefore, the current flowing through the first power supply line 110a is different from the current flowing through the second power supply line 110b.

In this embodiment, the voltage $V_L$ applied to the image pickup device 108 can also be obtained by the above described expression (6). Furthermore, the current $I_1$ flowing through the first power supply line 110a and the current $I_2$ flowing through the second power supply line 110b can be obtained by the following expressions (7) and (8), respectively.

$$I_1=(V_P-V_1)/PR1 \quad (7)$$

$$I_2=(V_P-V_2)/PR2 \quad (8)$$

That is, by detecting the voltage $V_1$ applied to an input point of the first power supply line 110a and the voltage $V_2$ applied to an input point of the second power supply line 110b by a voltage detector (not shown), the current $I_1$ and the current $I_2$ can be obtained. The scope controller 120 obtains the voltage $V_L$ applied to the image pickup device 108 by assigning the detected voltages $V_1$ and $V_2$ and the currents $I_1$ and $I_2$ calculated by the expressions (7) and (8) to the expression (6). Then, the scope controller 120 adjusts the voltage VP by controlling the first power supply P1 so that the voltage $V_L$ becomes equal to the reference voltage Vref or falls within the specification value range.

As described above, in this embodiment, the voltage $V_L$ having a high degree of accuracy can be applied to the image pickup device 108 regardless of the type of the electronic endoscope 100 as in the case of the first embodiment. Further, it is possible to decrease the number of power supplies in comparison with the first embodiment. As a result, reduction of cost and the number of parts as well as downsizing of the device can be realized.

Third Embodiment

Hereafter, an electronic endoscope 100B according to a third embodiment of the invention is described. In the electronic endoscope 100B according to the third embodiment, only a configuration of a power supply circuit 150B is different from the first embodiment, and the other configurations in the third embodiment are the same as those of the first embodiment. Therefore, in the following, explanations about the third embodiment focus on the feature of the third embodiment. In the following, to elements which are substantially the same as those of the first embodiment, the same reference numbers are assigned and explanations thereof will not be repeated.

Figure 4:
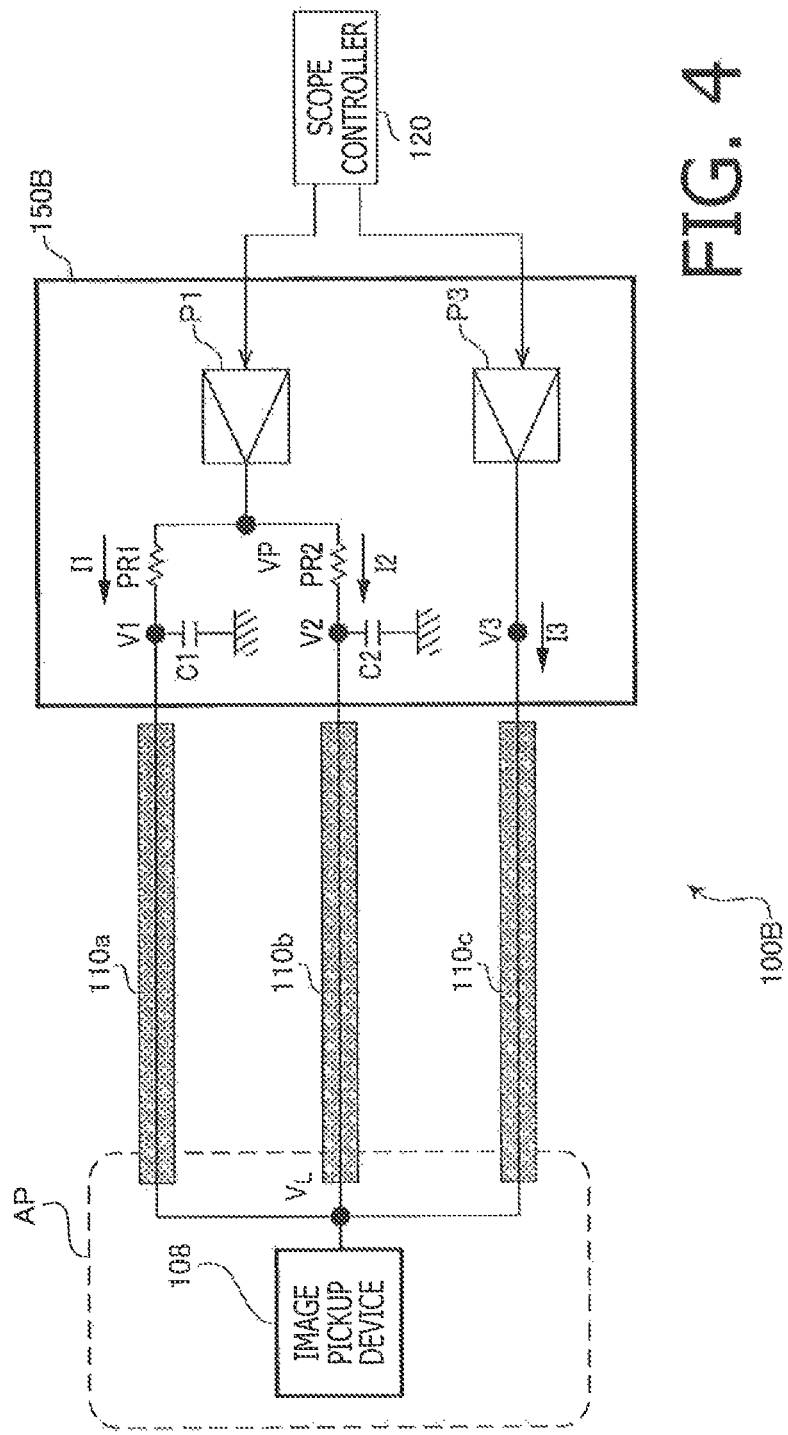
FIG. 4 illustrates a configuration of a power supply circuit according to a third embodiment of the invention.

FIG. 4 illustrates a configuration of the power supply circuit 150B according to the third embodiment. As shown in FIG. 4, the power supply circuit 150B includes the first power supply P1 and the third power supply P3 as in the case of the second embodiment, and the first power supply line 110a and the second power supply line 110b are connected to the first power supply P1. Specifically, the first power supply P1 is connected to the first power supply line 110a via the first resistor PR1, and is connected to the second power supply line 110b via the second resistor PR2. Resistances of the first resistor PR1 and the second resistor PR2 are different from each other (PR1≠PR2).

In this embodiment, a first capacitor C1 is provided at a connection point between the first power supply line 110a and the first resistor PR1. Further, a second capacitor C2 is provided at a connection point between the second power supply line 110b and the second resistor PR2. Each of the first capacitor C1 and the second capacitor C2 is grounded, and serves as a bypass capacitor to eliminate exogenous noise generated on the first lower supply line 110a and the second power supply line 110b.

As in the case of the second embodiment, in the third embodiment the scope controller 120 calculates the currents $I_1$ and $I_2$ from the expressions (7) and (8) by detecting the voltage $V_1$ applied to the input point of the first power supply line 110a and the voltage $V_2$ applied to the input point of the second power supply line 110b by a voltage detector (not shown). Then, the scope controller 120 obtains the voltage $V_L$ applied to the image pickup device 108 by assigning the obtained values to the expression (6), and adjusts the voltage $V_P$ by controlling the first power supply P1 so that the voltage $V_L$ becomes equal to the reference voltage Vref or falls within the specification value range.

As described above, according to the third embodiment, the same advantages as those of the first and second embodiments can be achieved. Furthermore, by providing the first and second capacitors C1 and C2, noise can be eliminated, and the voltages $V_1$ and $V_2$ can be detected more accurately. As a result, it becomes possible to apply the voltage $V_L$ having a higher degree of accuracy to the image pickup device 108.

Fourth Embodiment

Hereafter, an electronic endoscope 100C according to a fourth embodiment of the invention is described. In the electronic endoscope 100C according to the fourth embodiment, only a configuration of a power supply circuit 150C is different from the first embodiment, and the other configurations in the fourth embodiment are the same as those of the first embodiment. Therefore, in the following, explanations about the fourth embodiment focus on the feature of the fourth embodiment. In the following, to elements which are substantially the same as those of the first embodiment, the same reference numbers are assigned and explanations thereof will not be repeated.

Figure 5:
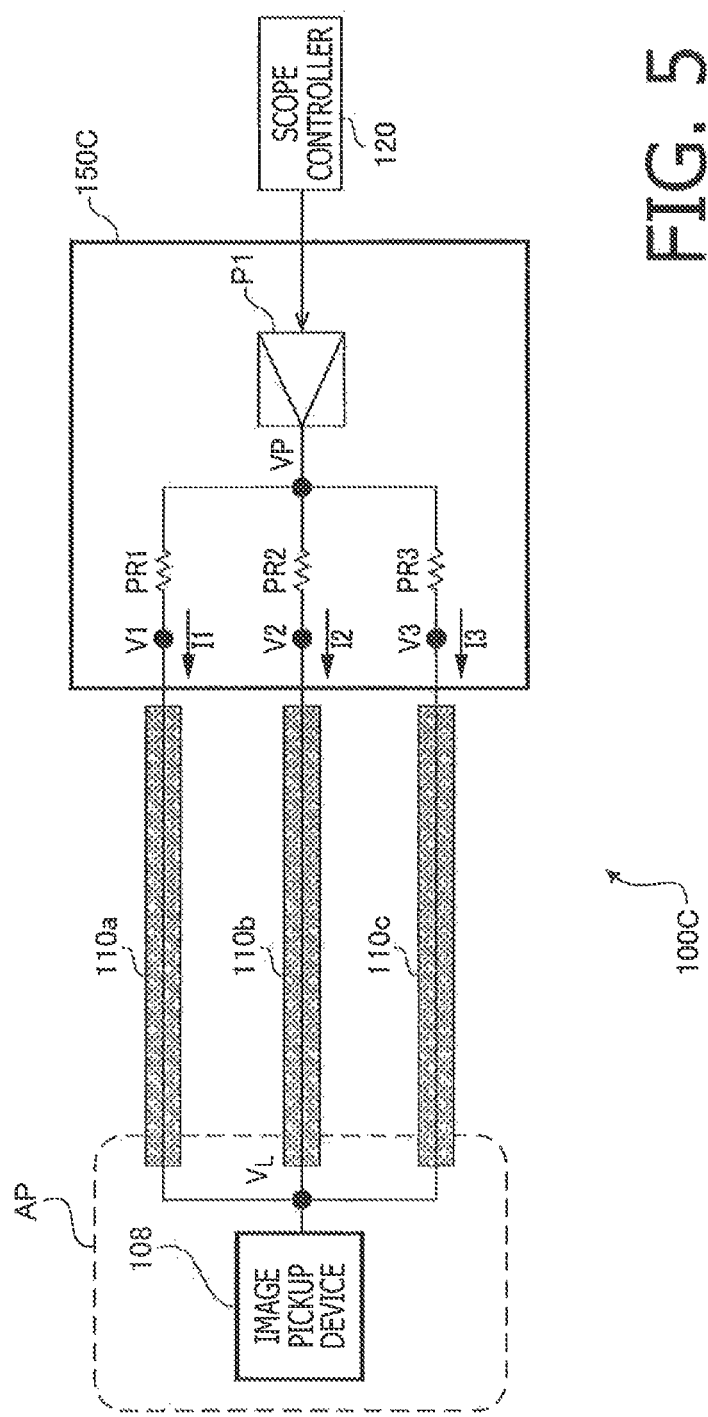
FIG. 5 illustrates a configuration of a power supply circuit according to a fifth embodiment of the invention.

FIG. 5 illustrates a configuration of the power supply circuit 150C according to the fourth embodiment. As shown in FIG. 5, the power supply circuit 150C according to the fourth embodiment includes the first power supply P1. The voltage VP generated by the first power supply P1 is transmitted to the image pickup device 108 via the first power supply line 110a, the second power supply line 110b and the third power supply line 110c.

Specifically, the first power supply P1 is connected to the first power supply line 110a via the first resistor PR1, and is connected to the second power supply line 110b via the second resistor PR2. Resistances of the first resistor PR1 and the second resistor PR2 are different from each other (PR1≠PR2). In the third embodiment, a third resistor PR3 is provided such that the first power supply P1 is connected to the third power supply line 110c via the third resistor PR3. The resistance of the third resistor PR3 is set appropriately depending on power supplied to the image pickup device 108.

As in the case of the second embodiment, in the fourth embodiment, the scope controller 120 detects the voltage $V_1$ applied to the input point of the first power supply line 110a and the voltage $V_2$ applied to the input point of the second power supply line 110b, and calculates the currents $I_1$ and $I_2$, from the expressions (7) and (8). Then, the scope controller 120 assigns the obtained values to the expression (6) to obtain the voltage $V_L$ applied to the image pickup device 108, and adjusts the voltage $V_P$ by controlling the first power supply P1 so that the voltage $V_L$ becomes equal to the reference voltage Vref or falls within the specification value range.

As described above, according to the fourth embodiment, the same advantages as those of the first and second embodiments can be achieved. Furthermore, the number of power supplies can be decreased further, and cost and the number of parts can be decreased further. As a result, the device can be downsized further. For measures against noise, in this embodiment bypass capacitors may be provided at connection points between the power supply lines and the resistors, respectively, as in the case of the third embodiment.

The foregoing is the explanation about the embodiments of the invention. The invention is not limited to the above described embodiments, but can be varied in various ways within the scope of the invention. For example, as an image pickup device, an image sensor (e.g., a CMOS (Complementary Metal Oxide Semiconductor) image sensor) other than a CCD may be used. In the tip portion AP of the electronic endoscope 100, parts having functions other than image pickup may be provided in addition to the image pickup device 108. Also, in this case, the power supply circuit 150 controls the power supply voltage supplied to the entire load disposed in the tip portion AP in the same way as that described in the embodiments.

Figure 6:
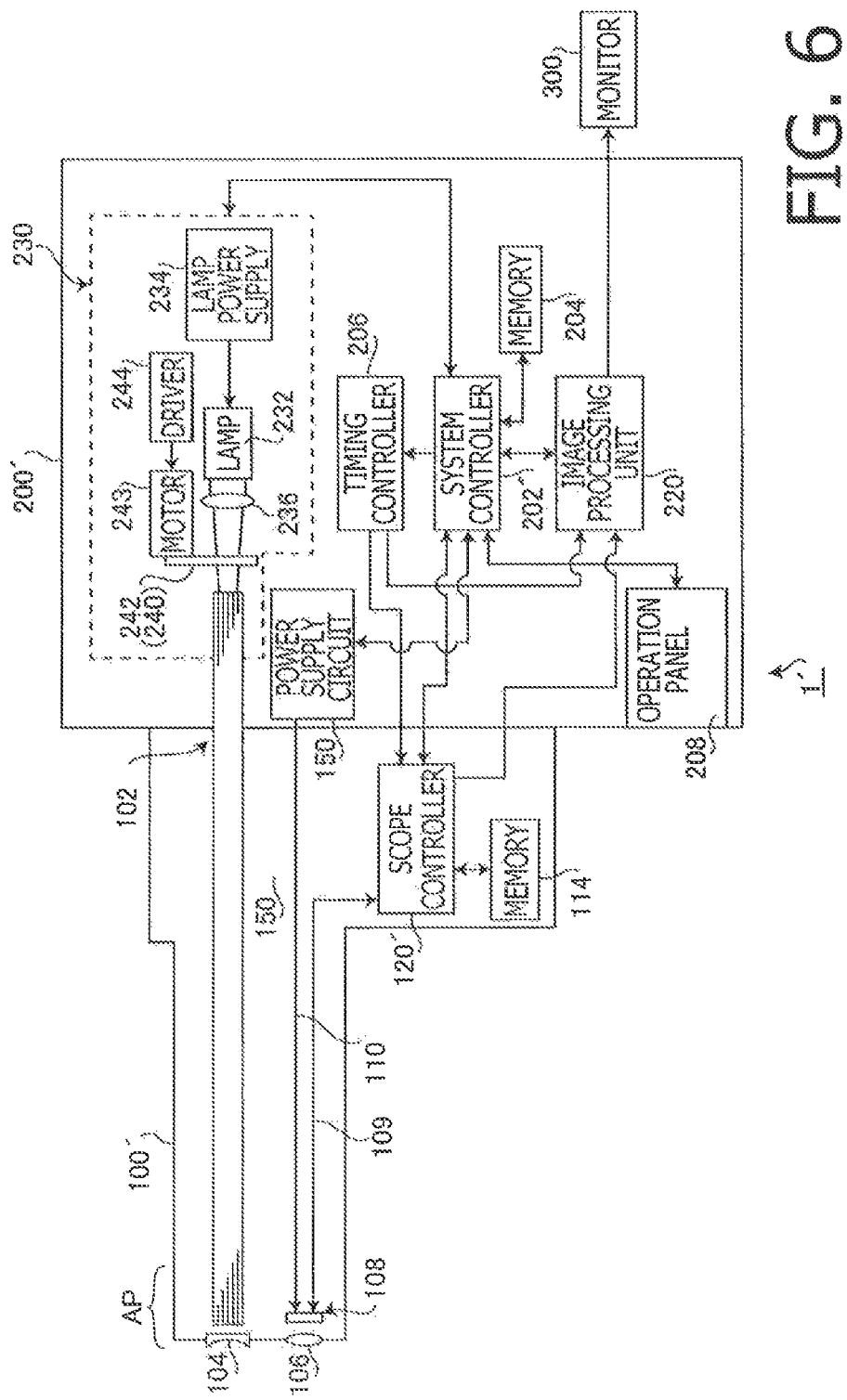
FIG. 6 illustrates a variation of a configuration of an electronic endoscope system according to the invention.

The power supply circuit 150 may be provided in the electronic endoscope processor 200, and the power supply circuit 150 may be controlled by the system controller 202 in place of the scope controller 120. FIG. 6 illustrates an example of such a variation of the electronic endoscope system 1. In an electronic endoscope system 1' shown in FIG. 6, the power supply circuit 150 is provided in an electronic endoscope processor 200', and the power supply voltage is supplied to the image pickup device 108 provided in the tip portion of an electronic endoscope 100'. In this case, the power supply circuit 150 is controlled by a system controller 202' in place of a scope controller 120'.

The electronic endoscope 100 is not limited for medical use, but may be configured as an endoscope for industrial use. Furthermore, the present invention is not limited to use in an endoscope, but may be applied to various types of devices having a power supply circuit supplying a power supply voltage to a load via a long cable.

In the above described embodiments, the cable having the same length and the same specifications (loss) is used for both of the first power supply line 110a and the second power supply line 110b; however, the invention is not limited to such a configuration. As long as the ratio (n) of a loss per a unit length and the ratio (m) of the length between the first power supply line 110a and the second power supply line 110b are known, the voltage $V_L$ applied to the image pickup device 108 can be obtained. Also in this case, only the ratio (n) of the loss per a unit length and the ratio (m) of the length between the first power supply line 110a and the second power supply line 110b are required, but concrete values of the loss per a unit length and the length of the first power supply line 110a and the second power supply line 110b are not required.

In the above described embodiment, power is supplied to the image pickup device 108 via three power supply lines; however, the invention is not limited to such a configuration. The invention may be applied to a configuration where at least two power supply lines are provided. The invention may be applied to a configuration where four or more power supply lines are provided. In the case where four or more power supply lines are provided, it is also possible to obtain the voltage $V_L$ applied to the image pickup device 108 from the voltages applied to two power supply lines and the currents flowing through the two power supply lines.

This application claims priority of Japanese Patent Application No. P2014-071142, filed on Mar. 31, 2014. The entire subject matter of the application is incorporated herein by reference.

What is claimed is:

1. An electronic endoscope, comprising:
an image pickup device disposed in a tip portion of the electronic endoscope;
a power supply circuit disposed in a proximal end portion of the electronic endoscope;
a controller disposed in the proximal end portion of the electronic endoscope; and
a cable connecting the image pickup device with the power supply circuit,
the cable comprising a first power supply line and a second power supply line, both of which serve to transmit a power supply voltage to the image pickup device,
the power supply circuit comprising at least one power supply that generates the power supply voltage and outputs the power supply voltage to the first power supply line and the second power supply line,
wherein the controller operates to:
obtain a voltage applied to the image pickup device based on a voltage applied to an input point of the first power supply line, a current flowing through the first power supply line, a voltage applied to an input point of the second power supply line, a current flowing through the second power supply line, a loss per a unit length of each of the first power supply line and the second power supply line, and a ratio of length between the first power supply line and the second power supply line; and
adjust the power supply voltage generated by the at least one power supply by controlling the at least one power supply so that a difference between the voltage applied to the image pickup device and a predetermined reference voltage is corrected.

2. An electronic endoscope, comprising:
an image pickup device;
a power supply circuit;
a cable connecting the image pickup device with the power supply circuit; and
a controller,
the cable comprising a first power supply line and a second power supply line, both of which serve to transmit a power supply voltage to the image pickup device,
the power supply circuit comprising at least one power supply that generates the power supply voltage and outputs the power supply voltage to the first power supply line and the second power supply line,
wherein the controller operates to:
obtain a voltage applied to the image pickup device based on a voltage applied to an input point of the first power supply line, a current flowing through the first power supply line, a voltage applied to an input point of the second power supply line, a current flowing through the second power supply line, a loss per a unit length of each of the first power supply line and the second power supply line, and a ratio of length between the first power supply line and the second power supply line; and
adjust the power supply voltage generated by the at least one power supply by controlling the at least one power supply so that a difference between the voltage applied to the image pickup device and a predetermined reference voltage is corrected.

3. The electronic endoscope according to claim 1, wherein the controller obtains the voltage applied to the image pickup device based on a following expression:

$$V_L = (n \times m \times I_2 \times V_1 - I_1 \times V_2)/(n \times m \times I_2 - I_1)$$

where $V_L$ denotes the voltage applied to the image pickup device, $V_1$ denotes the voltage applied to the input point of the first power supply line, $I_1$ denotes the current flowing through the first power supply line, $V_2$ denotes the voltage applied to the input point of the second power supply line, $I_2$ denotes the current flowing through the second power supply line, n denotes a ratio of a loss per a unit length between the first power supply line and the second power supply line and m denotes the ratio of length between the first power supply line and the second power supply line.

4. The electronic endoscope according to claim 1, wherein the first power supply line and the second power supply line are formed of a same wiring material having a same length and same specifications.

5. The electronic endoscope according to claim 1, wherein the controller obtains the voltage applied to the image pickup device based on a following expression:

$$V_L = (I_2 \times V_1 - I_1 \times V_2)/(I_2 - I_1)$$

where $V_L$ denotes the voltage applied to the image pickup device, $V_1$ denotes the voltage applied to the input point of the first power supply line, $I_1$ denotes the current flowing through the first power supply line, $V_2$ denotes the voltage applied to the input point of the second power supply line and $I_2$ denotes the current flowing through the second power supply line.

6. The electronic endoscope according to claim 1, wherein the image pickup device is a CMOS image sensor.

* * * * *